(12) United States Patent
Ledermann et al.

(10) Patent No.: US 9,880,127 B2
(45) Date of Patent: Jan. 30, 2018

(54) FAULT SIMULATOR FOR CHECKING THE DIAGNOSIS IMPLEMENTED IN A CONTROL DEVICE FOR A LAMBDA SENSOR IN AN INTERNAL COMBUSTION ENGINE

(71) Applicant: Robert Bosch GmbH, Stuttgart (DE)

(72) Inventors: Bernhard Ledermann, Weil der Stadt (DE); Claudius Bevot, Stuttgart (DE); Thomas Steinert, Weinstadt (DE)

(73) Assignee: ROBERT BOSCH GMBH, Stuttgart (DE)

( * ) Notice: Subject to any disclaimer, the term of this patent is extended or adjusted under 35 U.S.C. 154(b) by 152 days.

(21) Appl. No.: 14/417,310

(22) PCT Filed: Jul. 9, 2013

(86) PCT No.: PCT/EP2013/064454
§ 371 (c)(1),
(2) Date: Jan. 26, 2015

(87) PCT Pub. No.: WO2014/016109
PCT Pub. Date: Jan. 30, 2014

(65) Prior Publication Data
US 2015/0204814 A1    Jul. 23, 2015

(30) Foreign Application Priority Data
Jul. 25, 2012    (DE) .................. 10 2012 213 068

(51) Int. Cl.
*G01N 27/416*    (2006.01)
*G01M 15/10*    (2006.01)
(Continued)

(52) U.S. Cl.
CPC ..... *G01N 27/4163* (2013.01); *F02D 41/1495* (2013.01); *G01M 15/104* (2013.01);
(Continued)

(58) Field of Classification Search
CPC ........... F02D 2041/281; F02D 41/1456; F02D 41/1495; G01M 15/104; G01N 27/409;
(Continued)

(56) References Cited

U.S. PATENT DOCUMENTS 4,859,955 A    8/1989  Trethewey
5,091,698 A *  2/1992  Grabs ................ G01N 27/4065
                                                123/688

(Continued)

FOREIGN PATENT DOCUMENTS

CN          101793604 A        8/2010
DE       10 2006 008539        8/2008
(Continued)

OTHER PUBLICATIONS

Machine translation of DE 10 2008 027895 downloaded Aug. 18, 2016.*

(Continued)

*Primary Examiner* — Natalie Huls
(74) *Attorney, Agent, or Firm* — Norton Rose Fulbright US LLP; Gerard Messina

(57) ABSTRACT

A method for checking fault detection of a control device of an internal combustion engine for malfunction of a connected broadband lambda probe, including checking with a fault simulator between the lambda probe and the control device; to simulate faults of the broadband lambda probe, the fault simulator modifies electrical signals between the broadband lambda probe and the control device. A Nernst voltage of the lambda probe and a pump current of the control device are delivered to the fault simulator; the fault simulator delivers a pump current to the lambda probe and a Nernst voltage to the control device; to simulate faults of the lambda probe, the fault simulator modifies the Nernst voltage to the control device as to the Nernst voltage (Continued)

outputted from the lambda probe. Also described is a related fault simulator. The method and fault simulator monitor the fault detection of control devices for lambda probes.

9 Claims, 1 Drawing Sheet

(51) Int. Cl.
*G01N 27/409* (2006.01)
*G01N 27/41* (2006.01)
*F02D 41/14* (2006.01)
*G01N 27/419* (2006.01)
*G01R 31/00* (2006.01)
*F02D 41/28* (2006.01)
*G01N 33/00* (2006.01)

(52) U.S. Cl.
CPC ........... *G01N 27/409* (2013.01); *G01N 27/41* (2013.01); *F02D 41/1456* (2013.01); *F02D 2041/281* (2013.01); *G01N 27/419* (2013.01); *G01N 33/007* (2013.01); *G01R 31/007* (2013.01)

(58) Field of Classification Search
CPC .. G01N 27/41; G01N 27/4163; G01N 27/419; G01N 33/007; G01R 31/007
See application file for complete search history.

(56) References Cited

U.S. PATENT DOCUMENTS

| | | | | |
|---|---|---|---|---|
| 5,298,865 | A * | 3/1994 | Denz | F02D 41/1495 123/694 |
| 5,522,250 | A * | 6/1996 | Gee | G01D 18/00 73/1.07 |
| 6,960,290 | B2 * | 11/2005 | Akhavan | G01N 27/4175 204/401 |
| 7,010,773 | B1 | 3/2006 | Bartz et al. | |
| 7,499,789 | B2 * | 3/2009 | Toda | F02D 41/1495 123/688 |
| 7,899,606 | B2 * | 3/2011 | Bartick | F02D 41/1475 123/688 |
| 7,980,121 | B2 * | 7/2011 | Matsuoka | G01N 33/0037 73/114.69 |
| 2003/0080003 | A1 | 5/2003 | Akhavan et al. | |
| 2009/0056414 | A1 | 3/2009 | Matsuoka et al. | |

FOREIGN PATENT DOCUMENTS

| | | |
|---|---|---|
| DE | 10 2008 027895 | 2/2010 |
| DE | 10 2008 027896 | 2/2010 |
| EP | 1 860 565 | 11/2007 |
| JP | 2004-093957 A | 3/2004 |
| JP | 2004-095153 A | 3/2004 |
| JP | 2008-076191 A | 4/2008 |
| JP | 2011-149780 A | 8/2011 |
| WO | 01/60734 A1 | 8/2001 |
| WO | 01/90734 | 11/2001 |

OTHER PUBLICATIONS

Stefan Krauss : "Steuergeraete-Tests mit Fehlersimulation", Aug. 1, 2008, pp. 48-51, XP055088373, Retrieved from the Internet : URL :http://vector.com/portal/medien/cmc/press/PND/Test_VRT_ElektronikAutomotive_200811_PressArticle_DE.pdf [retrieved on Nov. 14, 2013].*

Marzinkowski, Tino, "Error stimulation with lambda probes" IAV GmbH, Gifhorn, Oct. 8, 2008.

* cited by examiner

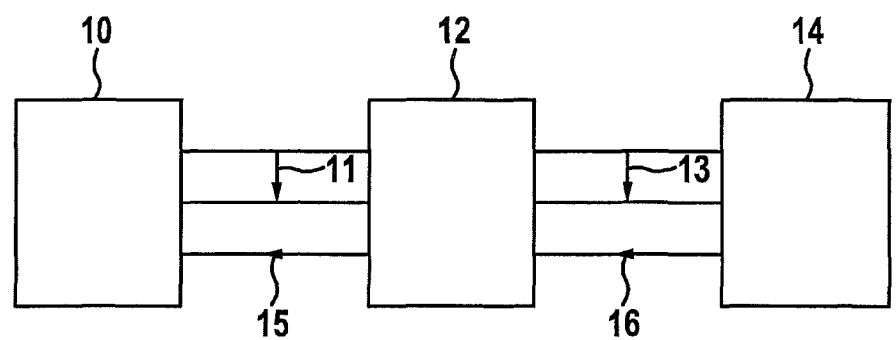

FAULT SIMULATOR FOR CHECKING THE DIAGNOSIS IMPLEMENTED IN A CONTROL DEVICE FOR A LAMBDA SENSOR IN AN INTERNAL COMBUSTION ENGINE

FIELD OF THE INVENTION

The present invention relates to a method for checking the fault detection of a control device of an internal combustion engine in the context of a malfunction of a connected broadband lambda probe, the check being carried out with a fault simulator disposed between the broadband lambda probe and the control device; and such that in order to simulate faults of the broadband lambda probe, the fault simulator specifically modifies electrical signals exchanged between the broadband lambda probe and the control device. The present invention further relates to a fault simulator for checking the fault detection of a control device of an internal combustion engine in the context of a malfunction of a connected broadband lambda probe, the fault simulator being disposed between the broadband lambda probe and the control device in order to simulate faults of the broadband lambda probe.

BACKGROUND INFORMATION

In order to optimize pollutant emissions and exhaust gas post-processing, lambda probes are used in modern internal combustion engines in order to identify the composition of the exhaust gas and to control the internal combustion engine. Lambda probes identify the oxygen content of the exhaust gas, which is used to regulate the air-fuel mixture delivered to the internal combustion engine and thus the exhaust gas lambda upstream from a catalytic converter. The delivery of air and fuel to the internal combustion engine is regulated via a lambda control loop in such a way that a composition of the exhaust gas which is optimal for exhaust gas post-processing by catalytic converters provided in the exhaust gas conduit of the internal combustion engine is achieved. In spark-ignited engines, regulation occurs as a rule to a lambda of 1, i.e. a stoichiometric ratio of air to fuel. The pollutant emissions of the internal combustion engine can thereby be minimized.

Various forms of lambda probes are in use. In contrast to two-point lambda probes, broadband lambda probes, also referred to as "continuous" or "linear" lambda probes, make it possible to measure the lambda value in the exhaust gas over a wide range around lambda=1. It is thus also possible, for example, to regulate an internal combustion engine to lean operation with excess air.

The sensor element of a broadband lambda probe has on the surface an opening through which exhaust gas enters. Adjacent to the entry opening is a porous layer through which the exhaust gas diffuses into a cavity. This cavity is separated from the external exhaust gas by an oxygen-ion-conducting electrolyte material. Located both externally on the electrolyte and on the cavity side are electrodes that are connected via cables to plug contacts. The electrolyte located therebetween is referred to as the "pump cell." Also located in the interior of the sensor element, separated from the cavity by the same electrolyte material, is a reference gas having a specific constant oxygen concentration. A further electrode, which is also connected to a plug contact, is in contact with the reference gas. The electrolyte between this electrode and the cavity-side electrode is referred to as the "measurement cell."

In accordance with the Nernst principle, an electrical voltage, hereinafter referred to as the "Nernst voltage" $UN0$, exists across the measurement cell, and is used to identify the concentration of oxidizing and reducing exhaust gas components in the cavity and in the reference gas. Since the concentration in the reference gas is known and invariable, the correlation comes down to the concentration in the cavity.

In order to operate the lambda probe, it must be connected via the plug to a corresponding electronic operating system, usually to an engine control device. The Nernst voltage $UN0$ is sensed via the electrodes and conveyed to the engine control device. Located in the engine control device is a control loop that holds the Nernst voltage across the measurement cell to a target value by driving a so-called "pump current" $IP$ through the pump cell. The control loop contains for this purpose a pump current regulator that is often also referred to, given its controlled variable, as a "Nernst voltage regulator." Because the current flow in the electrolyte occurs via oxygen ions, the oxygen concentration in the cavity is influenced. In order to keep the Nernst voltage $UN0$ constant in the equilibriated state, in the lean region ($\lambda > 1$) the amount of oxygen pumped out of the cavity must be exactly the same as the amount that diffuses away through the diffusion barrier. In the rich region ($\lambda < 1$), conversely, the amount of oxygen pumped into the cavity must be sufficient to compensate for the reducing exhaust gas molecules diffusing away. Given the fact that the oxygen balance in the cavity is kept constant by the pump current regulator, what follows from the diffusion equation is a linear relationship between the diffusion current (and thus the pump current) and the oxygen concentration in the exhaust gas. The pump current is measured in the engine control device or defined by the engine control device as a function of the measured Nernst voltage. The pump current represents a linear signal for the oxygen balance in the exhaust gas.

If a broadband lambda probe is faulty, that fact must be detected by the engine control device. Fault simulators, which are disposed during testing between the engine control device and the broadband lambda probe, are used nowadays in order to check whether an engine control device is detecting the relevant faults of a broadband lambda probe. The fault simulator behaves with respect to the engine control device like a broadband lambda probe having the faults that are to be checked. The engine control device must detect the relevant fault instances with no changes in software or applications.

One of the fault instances to be simulated is a change in the lambda signal of the broadband lambda probe. Here a delayed or distorted signal from the broadband lambda probe is specified to the engine control device. With fault simulators known at present, this fault is simulated by modifying the pump current, so as thereby to bring about changes in the broadband lambda probe and a corresponding reaction in the engine control device. These changes must be detected and displayed by the diagnostic function in the engine control device.

A change in the pump current in order to simulate a fault in the broadband lambda probe can cause the fault simulation itself to be too slow. This can cause the engine control device, for example, to react to real signal changes that are based on real changes in the composition of the exhaust gas, even though the fault simulator should suppress those changes.

In engine control devices in which an adjusted pump current represents the measured signal and no back-measurement of the resulting pump current occurs, the pump current is the output and the Nernst voltage UN0 is the input signal of the pump current regulator. Fault simulation by modification of the pump current signal here acts firstly on the broadband lambda probe. As a consequence, the Nernst voltage UN0 and thus the input signal of the pump current regulator changes. The known method for fault simulation via a change in the pump current has the disadvantage here that the change in the pump current arrives with a delay in the context of signal sensing in the engine control device. Real reactions by the broadband lambda probe to signal changes can therefore as a rule not be completely suppressed.

SUMMARY OF THE INVENTION

An object of the invention is to furnish a method for simulating faults of a broadband lambda probe, which method eliminated disruptive influences that become evident in the control device, for example, as a result of delayed reactions or signal transit times.

A further object of the invention is to furnish a corresponding fault simulator.

That object of the invention which relates to the method is achieved in that a Nernst voltage $UN0_{meas}$ of the broadband lambda probe and a pump current $IP_{EC}$ of the control device are delivered to the fault simulator; that the fault simulator delivers a pump current $IP_{probe}$ to the broadband lambda probe and a Nernst voltage $UN0_{adj}$ to the control device; and that in order to simulate faults of the broadband lambda probe, the fault simulator modifies the Nernst voltage $UN0_{adj}$ delivered to the control device with respect to the Nernst voltage $UN0_{meas}$ outputted from the broadband lambda probe.

According to a particular embodiment of the invention, provision can be made that in order to simulate a modified pump current $IP_{EC}$, the fault simulator modifies the Nernst voltage $UN0_{adj}$ delivered to the control device with respect to the Nernst voltage $UN0_{meas}$ outputted from the broadband lambda probe.

During ordinary operation of the internal combustion engine, the deviation of the Nernst voltage UN0 from the Nernst voltage target value is the input variable of the pump current regulator. The pump current IP is the output signal of the pump current regulator, and at the same time the measured variable that is further processed in the control device. The fault simulator can produce a change in the pump current signal by way of a change in the Nernst voltage $UN0_{adj}$ delivered to the control device with respect to the Nernst voltage $UN0_{meas}$ outputted from the broadband lambda probe. Because this change takes place earlier in time than the regulation action itself, no undesired reactions to changes in the pump current signal occur in the control device as a result of changes in the real exhaust gas. In addition, engine control devices in which an adjusted pump current represents the measured signal, and no back-measurement of the resulting pump current occurs, can be checked.

Different faults of the broadband lambda probe, for example a delayed response behavior due to aging effects or a distorted Nernst signal, can be simulated by the fact that in order to simulate faults, the fault simulator outputs to the control device a defined Nernst voltage $UN0_{adj}$ or a Nernst voltage $UN0_{adj}$ that is variable as a function of time.

Provision can be made that the fault simulator defines the defined Nernst voltage $UN0_{adj}$, or the Nernst voltage $UN0_{adj}$ that is variable as a function of time, in a manner independent of or dependent on the Nernst voltage $UN0_{meas}$ outputted from the broadband lambda probe. The outputted Nernst voltage $UN0_{adj}$ can be defined by a microcontroller provided in the fault simulator.

According to an exemplary embodiment of the invention, provision can be made that the pump current $IP_{probe}$ outputted to the broadband lambda probe corresponds to the pump current $IP_{EC}$ outputted from the engine controller, or that the pump current $IP_{probe}$ outputted to the broadband lambda probe is defined by the fault simulator on the basis of the Nernst voltage $UN0_{adj}$ outputted from the broadband lambda probe, or that the pump current $IP_{probe}$ outputted to the broadband lambda probe is defined by the fault simulator as a function of the pump current $IP_{EC}$ outputted from the control device.

The pump current $IP_{probe}$ outputted to the broadband lambda probe can be selected as a function of the fault to be simulated. If the pump current $IP_{probe}$ corresponds to the pump current $IP_{EC}$ outputted from the engine controller, the latter current can be looped from the engine controller through the fault simulator to the broadband lambda probe. If the pump current $IP_{probe}$ is defined by the fault simulator, the pump current $IP_{EC}$ furnished by the engine controller can be lowered in the fault simulator.

If the pump current $IP_{probe}$ outputted to the broadband lambda probe is defined by the fault simulator as a function of the pump current $IP_{EC}$ outputted from the control device, provision can be made that the pump current $IP_{probe}$ that is defined by the fault simulator as a function of the pump current $IP_{EC}$ and is outputted to the broadband lambda probe is defined to be higher or lower and/or delayed in time as compared with the pump current $IP_{EC}$.

In order to monitor the operational readiness of the broadband lambda probe, in particular in order to monitor its operating temperature, provision is made for regular identification of the internal resistance of the broadband lambda probe during ordinary operation. Provision can therefore be made that for an internal resistance measurement with respect to the control device, the fault simulator simulates a load and makes a corresponding voltage signal available.

Different faults of the broadband lambda probe can be simulated by the fact that the changes in the Nernst voltage $UN0_{adj}$ outputted from the fault simulator to the control device and in the pump current $IP_{probe}$ outputted to the broadband lambda probe, with respect to the Nernst voltage $UN0_{meas}$ outputted from the broadband lambda probe and with respect to the pump current $IP_{EC}$ outputted from the control device, occur simultaneously or separately from one another.

That object of the invention which relates to the fault simulator is achieved in that a Nernst voltage $UN0_{meas}$ of the broadband lambda probe and a pump current $IP_{EC}$ of the control device are delivered to the fault simulator; that a pump current $IP_{probe}$ is delivered to the broadband lambda probe, and a Nernst voltage $UN0_{adj}$ to the control device, by the fault simulator; and that the fault simulator is configured to modify the Nernst voltage $UN0_{adj}$ delivered to the control device with respect to the Nernst voltage $UN0_{meas}$ outputted from the broadband lambda probe. The fault simulator thus makes it possible to carry out the method described.

The invention will be explained in further detail below with reference to an exemplifying embodiment depicted in the FIGURE.

The FIGURE shows a fault simulator for checking the fault detection of a control device.

DETAILED DESCRIPTION

The FIGURE shows a fault simulator 12 for checking the fault detection of a control device 14. Fault simulator 12 is connected between a broadband lambda probe 10 and a control device 14. A Nernst voltage $UN0_{meas}$ 11 of broadband lambda probe 10 and a pump voltage $IP_{EC}$ 16 of control device 14 are delivered to fault simulator 12. Fault simulator 12 delivers a pump current $IP_{probe}$ 15 to broadband lambda probe 10, and a Nernst voltage $UN0_{adj}$ 13 to control device 14. The signals are indicated by corresponding arrows; the number of signal lines depicted is limited to the number necessary for illustration of the invention.

Fault simulators 12 are used in order to test specific fault scenarios in broadband lambda probes 10. Fault simulator 12 is connected for this purpose between broadband lambda probe 10 and the associated control device 14. Fault simulator 12 behaves with respect to control device 14 like a broadband lambda probe 10 having the faults to be checked, while broadband lambda probe 10 continues to be operated. Control device 14 must detect the faults defined by the fault simulator with no changes in software or in applications.

One fault instance to be simulated is a change in the lambda signal of broadband lambda probe 10, so that a delayed or distorted lambda signal is simulated to control device 14. With known fault simulators 12, the pump current IP is modified for this purpose, so as thereby to produce changes in broadband lambda probe 10. These modifications must be detected by control device 14 by way of a diagnostic function.

The modification of pump current IP in order to simulate a fault of broadband lambda probe 10 can cause the fault simulation itself to be too slow. The result in control device 14 can be that the control device reacts, for example, to real signal changes in the context of a corresponding real change in the exhaust gas composition, even though fault simulator 12 should suppress that change.

Provision is therefore made according to the present invention that the fault simulation is carried out by fault simulator 12 on the basis of the Nernst voltage UN0. For this purpose, fault simulator 12 also interrupts the delivery to control device 14 of the Nernst voltage $UN0_{meas}$ 11 outputted from broadband lambda probe 10, and outputs a correspondingly modified Nernst voltage $UN0_{adj}$ 13 to control device 14. Fault simulator 12 can thus produce a change in the pump current $IP_{EC}$ 16 by correspondingly modifying the Nernst voltage $UN0_{adj}$ 13. Because this change takes place earlier in time than the regulation action itself, no undesired reactions to changes in the pump current signal due to a change in the real exhaust gas are visible in control device 14.

Control device 14 can arbitrarily define the outputted Nernst voltage $UN0_{adj}$ 13, and in particular a change over time in the Nernst voltage $UN0_{adj}$ 13. This can be accomplished by way of a microcontroller provided in fault simulator 12, for example as a function of the measured Nernst voltage $UN0_{meas}$ or independently thereof.

The pump current $IP_{EC}$ 16 thereupon calculated and outputted from control device 14 can be conveyed directly by fault simulator 12 to broadband lambda probe 10. Alternatively thereto, the pump current $IP_{EC}$ 16 can be lowered in fault simulator 12 with no effect on broadband lambda probe 10. In this case broadband lambda probe 10 is impinged upon by a pump current $IP_{probe}$ 15 that has been calculated in fault simulator 12 on the basis of Nernst voltage $UN0_{meas}$ 11. A third possibility is to manipulate pump current $IP_{probe}$ 15 as a function of pump current $IP_{EC}$ 16 and convey it to broadband lambda probe 10. Pump current $IP_{probe}$ 15 can be higher, lower, or delayed in time with respect to pump current $IP_{EC}$ 16.

What is claimed is:

1. A method for checking a fault detection of a control device of an internal combustion engine for a malfunction of a connected broadband lambda probe, the method comprising:

checking for the fault detection with a microcontroller of a fault simulator disposed between the broadband lambda probe and the control device;

modifying, to simulate faults of the broadband lambda probe, via the microcontroller, electrical signals exchanged between the broadband lambda probe and the control device, a Nernst voltage of the broadband lambda probe and a pump current of the control device being delivered to the microcontroller; and delivering, via the microcontroller, a pump current to the broadband lambda probe and a Nernst voltage to the control device;

wherein to simulate faults of the broadband lambda probe, the microcontroller interrupts delivery of the Nernst voltage from the broadband lambda probe to the control device, and delivers to the control device a modified Nernst voltage while the broadband lambda probe continues to operate, wherein the modified Nernst voltage is modified with respect to the Nernst voltage received by the microcontroller from the broadband lambda probe, wherein to simulate a modified pump current, the microcontroller delivers the modified Nernst voltage to the control device, and wherein to simulate faults, the microcontroller outputs to the control device a defined Nernst voltage or a Nernst voltage that is variable as a function of time.

2. The method of claim 1, wherein the microcontroller defines the defined Nernst voltage or the Nernst voltage that is variable as a function of time, independent of or dependent on the Nernst voltage outputted from the broadband lambda probe.

3. The method of claim 1, wherein the pump current outputted to the broadband lambda probe corresponds to the pump current outputted from the engine controller, or the pump current outputted to the broadband lambda probe is defined by the microcontroller based on the Nernst voltage outputted from the broadband lambda probe, or the pump current outputted to the broadband lambda probe is defined by the microcontroller as a function of the pump current outputted from the control device.

4. The method of claim 3, wherein the pump current that is defined by the microcontroller as a function of the pump current outputted from the control device is outputted to the broadband lambda probe and is defined by the microcontroller to be higher or lower and/or delayed in time as compared with the pump current outputted from the control device.

5. The method of claim 1, wherein for an internal resistance measurement with respect to the control device, the microcontroller simulates a load and makes a corresponding voltage signal available.

6. The method of claim 1, wherein the changes in the Nernst voltage outputted from the microcontroller to the control device and in the pump current outputted to the broadband lambda probe, with respect to the Nernst voltage outputted from the broadband lambda probe and with respect to the pump current outputted from the control device, occur simultaneously or separately from one another.

7. A fault simulator for checking a fault detection of a control device of an internal combustion engine for a malfunction of a connected broadband lambda probe, comprising:
 a microcontroller disposed between the broadband lambda probe and the control device to simulate faults of the broadband lambda probe, wherein a Nernst voltage of the broadband lambda probe and a pump current of the control device is deliverable to the microcontroller, wherein a pump current is deliverable to the broadband lambda probe and a Nernst voltage is deliverable to the control device by the microcontroller;
 wherein the microcontroller is configured to interrupt delivery of the Nernst voltage from the broadband lambda probe to the control device, and deliver to the control device a modified Nernst voltage while the broadband lambda probe continues to operate, wherein the modified Nernst voltage is modified with respect to the Nernst voltage received by the microcontroller from the broadband lambda probe, and
 wherein to simulate a modified pump current, the modified Nernst voltage delivered to the control device is variable with respect to the Nernst voltage outputted from the broadband lambda probe, the Nernst voltage or a Nernst voltage that is variable as a function of time being outputtable to the control device.

8. The method of claim 1, wherein modifying the Nernst voltage delivered to the control device with respect to the Nernst voltage outputted from the broadband lambda probe reduces disruption experienced by the control device from at least one of delayed reactions and signal transit times.

9. The fault simulator of claim 7, wherein modifying the Nernst voltage delivered to the control device with respect to the Nernst voltage outputted from the broadband lambda probe reduces disruption experienced by the control device from at least one of delayed reactions and signal transit times.

\* \* \* \* \*